United States Patent [19]

Greve et al.

[11] 4,289,765
[45] Sep. 15, 1981

[54] 4-AMINOPYRIDINES AND MEDICAMENTS CONTAINING THE SAME

[75] Inventors: Wilfried Greve; Heinzgeorg von Schuh, both of Wiesbaden; Hiristo Anagnostopulos, Taunusstein, all of Fed. Rep. of Germany

[73] Assignee: Hoechst Aktiengesellschaft, Frankfurt, Fed. Rep. of Germany

[21] Appl. No.: 109,913

[22] Filed: Jan. 7, 1980

[30] Foreign Application Priority Data

Jan. 8, 1979 [DE] Fed. Rep. of Germany ....... 2900504

[51] Int. Cl.³ ................. A61K 31/44; A61K 31/535; A61K 31/54; C07D 213/61; C07D 213/85; C07D 413/04; C07D 417/04
[52] U.S. Cl. ................. 424/246; 260/244.4; 424/248.4; 424/250; 424/251; 424/263; 424/267; 544/3; 544/54; 544/55; 544/58.2; 544/58.6; 544/60; 544/63; 544/96; 544/127; 544/131; 544/238; 544/333; 544/360; 546/193; 546/194; 546/270; 546/275; 546/278; 546/279; 546/280; 546/281; 546/289; 546/304; 546/312
[58] Field of Search .................... 260/244.4; 424/246, 424/248.4, 250, 251, 263, 267; 546/193, 194, 270, 275, 278, 279, 280, 281, 289, 304, 312, 307; 544/3, 54, 55, 58.2, 58.6, 60, 63, 96, 127, 131, 238, 333, 360

[56] References Cited

U.S. PATENT DOCUMENTS 3,517,021 6/1970 Marschik et al. .................... 546/289
3,547,935 12/1970 Diehl et al. ..................... 546/312 X
3,926,611 12/1975 Tomlin et al.

*Primary Examiner*—Richard Raymond
*Attorney, Agent, or Firm*—Curtis, Morris & Safford

[57] ABSTRACT

4-Aminopyridines of the formula

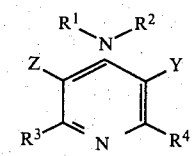

in which
$R^1$ is hydrogen or alkyl of up to 6 carbon atoms and
$R^2$ represents (a) alkyl of up to 6 carbon atoms substituted up to three times with at least one radical from the group of halogen and hydroxyl, with formyl acetalized with an alcohol of up to 3 carbon atoms, alkylthio of up to 3 carbon atoms, phenylthio or the corresponding alkyl- and phenyl-sulfoxy and sulfone groups, the phenyl ring optionally carrying in each case up to three substituents from the group of alkyl, alkyl halide, alkoxy, mono- or dialkylamino having each up to 4 carbon atoms in each alkyl radical, halogen, nitro, amino and hydroxy, or (b) phenylalkyl or diphenyl-alkyl of up to 6 carbon atoms in the linear or branched alkyl moiety, the phenyl rings optionally being substituted up to three times with at least one radical from the group of alkyl, alkoxy, alkyl halide with up to 4 carbon atoms each, halogen, amino, hydroxy, nitro, the sulfamoyl group and the methylene dioxy radical, or
$R^1$ and $R^2$, together with the nitrogen atom present in the 4-position, form a five- to seven-membered heterocyclic ring optionally substituted with alkyl of up to 2 carbon atoms and including up to two hetero-atoms, the second hetero-atom being oxygen, sulfur optionally carrying up to two oxygen atoms, or nitrogen, and
$R^3$ and $R^4$ which may be identical or different, each represent alkyl of up to 9 carbon atoms, one of the two radicals optionally also being hydrogen,
Y is a nitro or a cyano group, and
Z stands for hydrogen or halogen,
and the physiologically acceptable salts of these compounds, processes for their preparation and medicaments made thereof.

8 Claims, No Drawings

4-AMINOPYRIDINES AND MEDICAMENTS CONTAINING THE SAME

In U.S. Pat. No. 3,547,935 there has been described the preparation of herbicidally active 3-nitropyridines carried out, for example, by reacting substituted 4-chloro-3-nitropyridines with diethyl- or di-n-propylamine. However, compounds of this kind with additional alkyl substituents in the 2- and/or 6-positions have not been disclosed in this Patent Specification.

Surprisingly, it has now been found that by introducing suitable primary and secondary amines into the 4-position of 2,6-dialkyl-3-nitro (or cyano)-pyridines there are obtained compounds with excellent pharmacological properties, in which the bronchospasmolytic action is the most prominent feature. Said compounds represent a novel type of structure among the bronchospasmolytic agents known so far.

Besides, the compounds of the invention are appropriate as ideal starting compounds for the synthesis of further valuable drugs.

Thus, the present invention relates to substituted 4-aminopyridines including the acid addition salts thereof, a process for preparing them and their use as medicaments.

Hence, the subject of the invention are pyridines carrying several substituents and corresponding to the formula I (cf. claim 1), in which $R^1$ is hydrogen or alkyl of up to 6 carbon atoms and $R^2$ represents (a) alkyl of up to 6 carbon atoms substituted up to three times with at least one radical from the group of halogen and hydroxyl, with formyl acetalized with an alcohol of up to 3 carbon atoms, alkylthio of up to 3 carbon atoms, phenylthio or the corresponding alkyl- and phenyl-sulfoxy and sulfone groups, the phenyl ring optionally carrying in each case up to three substituents from the group of alkyl, alkyl halide, alkoxy, mono- or dialkylamino having each up to 4 carbon atoms in each alkyl radical, halogen, nitro, amino and hydroxy, or (b) phenylalkyl or diphenyl-alkyl of up to 6, preferably up to 4 carbon atoms in the linear or branched alkyl moiety, the phenyl rings optionally being substituted up to three times with at least one radical from the group of alkyl, alkoxy, alkyl halide with up to 4 carbon atoms each, halogen, amino, hydroxy, nitro, the sulfamoyl group and the methylene dioxy radical, or $R^1$ and $R^2$, together with the nitrogen atom present in the 4-position, form a five- to seven-membered heterocyclic ring optionally substituted with alkyl of up to 2 carbon atoms and including up to two hetero-atoms, the second hetero-atom being oxygen, sulfur optionally carrying up to two oxygen atoms, or nitrogen, and $R^3$ and $R^4$ which may be identical or different, each represent alkyl of up to 9, preferably up to 7 and especially up to 4 carbon atoms, one of the two radicals optionally also being hydrogen, Y is a nitro or a cyano group, and Z stands for hydrogen or halogen, and the physiologically acceptable addition salts thereof with organic or inorganic acids.

Preference is given to those compounds of the formula I as well as the salts thereof in which $R^3$ and $R^4$ each represent alkyl of up to 4 carbon atoms, Y is a nitro or a cyano group, and Z is hydrogen, and either $R^1$ and $R^2$ together with the nitrogen atom present in the 4-position form a morpholine or thiomorpholine ring, or $R^1$ is hydrogen or alkyl of up to 4 carbon atoms, $R^2$ is alkyl of up to 4 carbon atoms being substituted by halogen, alkylthio of up to 3 carbon atoms or a phenylthio group optionally substituted, or $R^1$ is hydrogen, $R^2$ is benzyl, the $CH_2$ group of which may be substitutd by methyl and the phenyl ring of which may be substituted by alkoxy of up to 2 carbon atoms, halogen, the sulfamoyl group or the methylene dioxy radical.

The compounds of the formula I are novel and possess valuable pharmacological and above all bronchospasmolytic properties.

Another subject of the invention is a process for preparing the 4-aminopyridines of the invention, which comprises reacting a compound of the formula II (cf. claim 6) in common manner with an amine of the formula $R^1$—NH—$R^2$ (III), $R^1$, $R^2$, $R^3$ and $R^4$, Y and Z being defined as above and X being halogen, and isolating the products thus obtained. Compounds of the formula I, in which $R^2$ contains a halogen atom bound to alkyl, may also be prepared by halogenating products of the formula I, in which $R^2$ contains a hydroxyl group bound to alkyl, in accordance with common methods; compounds of the formula I, in which $R^2$ contains an alkylthio, phenylthio, sulfoxy or sulfone group, may also be prepared by reacting compounds of the formula II, in which $R^2$ contains a halogen atom bound to alkyl, with mercaptans of the formula HS-$R^5$ (IV), in which $R^5$ represents alkyl of up to 3 carbon atoms or phenyl optionally substituted by the radicals specified in $R^2$ under (a), and by subsequently oxydizing the compounds thus obtained to give sulfoxides or sulfones. In all cases the final products I may be isolated either in the form of the free bases or may be converted with appropriate acids into physiologically acceptable acid addition salts.

For the preparation of the acid addition salts there may be mentioned, for example, hydrohalic acids, especially hydrochloric acid, furthermore sulfuric, phosphoric, acetic, lactic, maleic, fumaric, oxalic, tartaric, citric, gluconic, p-toluene-sulfonic, methane-sulfonic and cyclohexylamidosulfonic acid.

The starting compounds of formulae II to IV are in most cases known from literature or may easily be prepared according to methods known from literature.

Suitable compounds of formula II are, for example, the symmetrical 2,6-dialkyl-4-halogen-3-nitro-pyridines, such as 4-chloro-2,6-dimethyl-3-nitropyridine (P. NantkaNamirski, Acta Polon. Pharm. 18, (1961)) and 4-chloro-2,6-dipropyl-3-nitropyridine, which may be obtained from acylacetic acid esters via the 6-alkyl-3-acyl-2,3-dihydro-2,4-dioxy-pyranes by a reaction with ammonia, subsequent nitration in the 3-position and halogenation of the 4-position, 2,6-dialky-3-cyano-4-halopyridines, such as 4-chloro-3-cyano-2,6-dimethyl-pyridine (T. Kato et al., Yakugaku Zasshi 91, 740 (1971)) or 2,6-dialkyl-4,5-dihalogen-3-nitropyridines, such as 5-bromo-4-chloro-2,6-dimethyl-3-nitropyridine (P. Nantka-Namirski, Acta Polon.Pharm. 18, 449 (1961)), as well as the unsymmetrical 2,6-dialkyl-4-halogen-3-nitropyridines, such as 2-hexyl-6-methyl- or 2-methyl-6-hexyl-4-chloro-3-nitro-pyridine, which may be synthesized, for example, by a reaction of corresponding 3-alkyl-3-aminoacrylic acid esters with diketene (T. Kato et al., Yakugaku Zasshi 91, 740 (1971)) or any acylacetic acid esters and subsequent saponification, decarboxylation, nitration, isomer separation and halogenation.

Suitable amines according to formula III are, for example, morpholine, thiomorpholine, benzylamine, p-fluorobenzylamine, p-sulfamoylbenzylamine, piperonylamine, p-methoxybenzylamine, (+) 1-phenylethylamine and (−) 1-phenylethylamine, 2-aminoethanol, 3-aminopropanol, 2-fluoroethylamine, 3-fluoropropylamine, 2,2,2-trifluoroethylamine and N-(2-hydroxyethyl)-ethylamine.

Suitable mercaptans according to formula IV are, for example, methyl- and ethylmercaptan, thiophenol, 4-chloro-, 4-fluoro-, 4-amino-, 4-dimethylamino-, 4-methyl-, 4-methoxy-, 3,4-dichloro-, 3-methyl-4-methoxy- and 3-trifluoromethyl thiophenol.

The reaction of compounds of the formula II with the amines of the formula III is suitably carried out in a solvent or dispersing agent.

For this purpose, there are suitable alcohols, such as methanol, ethanol, isopropanol, n-propanol, the various butanols as well as mixtures of the same or their mixtures with water, ethers, such as tetrahydrofuran and dioxan, aprotic solvents, such as pyridine, dimethyl formamide, dimethyl acetamide, dimethyl sulfoxide and hexamethyl-phosphoric acid triamide or hydrocarbons, such as benzene, toluene and xylene.

The condensation reaction is executed by using advantageously at least twice the molar amount of the amine employed in the respective case; it is also possible to use equimolar amounts of the two reactants, however, in this case the addition of an acid binding agent is recommended, for example, an alkali metal or alkaline earth metal hydroxide or -carbonate or an organic base, such as triethylamine, in an amount which is at least stoichiometrical. The reaction in the first step is generally carried out at a temperature of from 0° C. to the boiling point of the respective solvent, preferably between 20° and 100° C., the reaction period being in the range of from some minutes to several hours.

For the halogenation, especially the chlorination of compounds according to formula I, which in $R^2$ carry a hydroxyl group bound to alkyl, there are used suitable halogenating, especially chlorinating agents, such as phosphoroxychloride, phosphorus pentachloride or mixtures thereof, a combination of triphenyl phosphine with carbon tetrachloride, thionyl chloride or bromide. As solvents there are suitable for this purpose, besides the halogenating agents themselves, above all those which are inert towards the reactants under the reaction conditions, for example, hydrocarbons, such as hexane, benzene and toluene or halogenated hydrocarbons, such as dichloromethane, chloroform, carbon tetrachloride and chlorobenzene.

The halogenation reactions are generally carried out at a temperature of from +10° to 100° C., preferably between 20° and 70° C., the reaction period also optionally being in the range of from some minutes to several hours.

For the further reaction of compounds of the formula I containing a halogen atom in $R^2$ with the mercaptans of the formula IV, there are used predominantly water, alcohols, such as methanol, ethanol, propanol, isopropanol or the mixtures thereof with water, dimethyl formamide, dimethyl acetamide, dimethyl sulfoxide, hexamethyl-phosphoric triamide or pyridine as solvents. This reaction with the mercaptans is carried out advantageously in the presence of an acid-binding agent, such as an alkali metal or alkaline earth metal hydroxide, suitably at a temperature of from 0 to 150, preferably from 50° to 100° C.

For the oxidation of compounds of the formula I with a sulfur-containing $NR^1R^2$ group to give sulfoxides or sulfones there are suitable, for example, oxidizing agents, such as sodium metaperiodate, nitric acid or possibly also elementary chlorine, the oxidizing agent itself or water serving as solvent and the reaction temperatures generally being in the range of from −20 to 100, preferably from 0° to 70° C.

As alkyl radicals for $R^1$, $R^2$, $R^3$ and $R^4$ there may be mentioned in each case for example methyl, ethyl, propyl, isopropyl, n-, iso- or tert.-butyl, linear or branched pentyl or hexyl, and for $R^3$ and $R^4$ additionally linear or branched heptyl, octyl or nonyl, for example the diisobutyl radical or the triisopropyl radical. The heterocyclic radicals which together may form $R^1$ and $R^2$ are for example saturated, such as the morpholine and the thiomorpholine ring, furthermore, the pyrrolidine ring, the piperidine ring and the ring of the formula

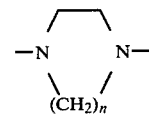

in which n is 1, 2 or 3, or unsaturated, such as the 4—H-1,4-thiazine ring.

In all other cases there may be mentioned as halogen for example chlorine, bromine and fluorine, with X in the formula II preferably being chlorine or bromine, and aliphatically bound halogen preferably being fluorine or chlorine.

Due to their pharmacological properties, the novel 4-aminopyridines of the formula I and the physiologically acceptable salts thereof may be used as medicaments, especially those for the treatment of diseases affecting the respiratory system, said compounds either being administered as such, for example in the form of microcapsules, or in combination with suitable carrier substances.

Thus, another subject of the invention are medicaments which contain at least one compound of the formula I as active ingredient, optionally in the form of one of their physiologically acceptable acid addition salts. The preparations may be administered orally and parenterally. Suitable solid or liquid galenic preparations are, for example, granules, powders, tablets, dragees, capsules, suppositories, syrups, emulsions, suspensions, drops or injectable solutions as well as preparations with a protracted release of the active substance. As carrier substances that are commonly used, there may be mentioned, for example, magnesium carbonate, various types of sugar, starch, cellulose derivatives, gelatin, animal and vegetable oils, polyethylene glycols and solvents.

The necessary dosage in the treatment of an adult patient suffering from bronchial obstruction is generally in the range of from 30 to 150 mg/day, preferably from 40 to 100 mg/day, when administered orally. In the case of intravenous administration, the dosage is generally from 10 to 50 mg/day, preferably from 15 to 30 mg/day.

A special application of the compounds according to formula I and the salts thereof is involved in the combination with other appropriate active substances, for example antiallergic agents, antitussives, secretolytic agents, sedatives, peripheral vasotherapeutic agents, antihistamines and also other bronchospasmolytic agents, such as $\beta_2$-sympathomimetic agents or parasympatholytics.

The following Examples illustrate the invention.

EXAMPLES

The structure of the compounds described in the following has been proved by ultimate analysis and $^1$H—NMR spectra.

1.

4-(2,6-Dimethyl-3-nitro-4-pyridyl)-thiomorpholinohydrochloride 37.4 Grams (0.2 mol) of 4-chloro-2,6-dimethyl-3-nitro-pyridine, 26 g (0.25 mol) of thiomorpholine and 75 ml (0.5 mol) of triethylamine are dissolved in 100 ml of isopropanol and refluxed for 10 hours. Upon completion of the reaction the solvent is removed under reduced pressure. The residue is dissolved in chloroform and shaken out three times with water. The chloroform phase is dried, concentrated and dissolved in ethanol for conversion into the hydrochloride, thereafter ethanolic hydrochloric acid is added. The precipitate is filtered off with suction and recrystallized from methanol. The yield obtained is 44.8 g (77.3% of the theory), and the melting point is 240° C. (with decomposition).

$C_{11}H_{16}Cl\ N_3O_2S$ (molec. weight 289.79)
Analysis:
Calculated: C: 45.59%; H: 5.57%; Cl: 12.23%; N: 14.50%; S: 11.06%.
Found: C: 45.47%; H: 5.47%; Cl: 12.16%; N: 14.49%; S: 11.16%.

2.

4-(5-Bromo-2,6-dimethyl-3-nitro-4-pyridyl)-thiomorpholine 11.68 Grams (0.044 mol) of 5-bromo-4-chloro-2,6-dimethyl-3-nitro-pyridine and 9.11 g (0.088 mol) of thiomorpholine are heated at boiling point for 18 hours in 50 ml of isopropanol. Upon completion of the reaction the solvent is removed, the residue is digested with water, and the yellow precipitate is filtered off with suction and recrystallized from isopropanol.

Yield: 9.96 g (68.1% of the theory); melting point 138° C.

$C_{11}H_{14}Br\ N_3O_2S$ (MW=332.23)
Analysis:
Calculated: C: 39.77%; H: 4.25%; Br: 24.10%; N: 12.65%; S: 9.65%.
Found: C: 40.00%; H: 4.17%; Br: 23.78%; N: 12.51%; S: 9.43%.

3.

4-(5-Bromo-2,6-dimethyl-4-pyridyl)-thiomorpholine-S-oxide hydrochloride 3.2 Grams (0.015 mol) of sodium metaperiodate are dissolved in water, and at 0° C. 4.7 g (0.014 mol) of 4-(5-bromo-2,6-dimethyl-3-nitro-4-pyridyl)-thiomorpholine of Example 2 are added, while stirring. Thereafter the reaction mixture is slowly brought to room temperature, and stirring is continued for another 22 hours at this temperature. The precipitate is filtered off with suction and the filtrate is extracted with methylene chloride. The organic phase is dried and concentrated. The residue is dissolved in ethanol and mixed with ethanolic hydrochloric acid.

Yield: 4.24 g (78.7% of the theory); melting point 170° C.

$C_{11}H_{15}Br\ Cl\ N_3O_3S$ (MW=384.69)
Analysis:
Calculated: C: 34.34%; H: 3.93%; Cl: 9.22%; N: 10.93%; S: 8.33%;
Found: C: 34.33%; H: 3.97%; Cl: 8.97%; N: 10.85%; S: 8.38%.

4.

4-(2,6-Dimethyl-3-nitro-4-pyridyl)-thiomorpholine-S,S-dioxide hydrochloride

5 Grams (0.02 mol) of 4-(2,6-dimethyl-3-nitro-4-pyridyl)-thiomorpholine of Example 1 are added portionwise to 50 ml of ice-cooled fuming nitric acid (d=1.5). The mixture is slowly brought to room temperature and then heated at 70° C. for 6 hours. After cooling it is carefully diluted with water and neutralized with sodium hydroxide solution, while cooling with ice. The neutral aqueous solution is concentrated, mixed once again with water, and the insoluble part is filtered off, recrystallized from methanol and converted with ethanolic hydrochloric acid into the hydrochloride.

Yield: 2 g (31% of th.); melting point 255° C. (decomp.)

$C_{11}H_{16}Cl\ N_3O_4S$ (MW=321.78)
Analysis:
Calculated: C: 41.06%; H: 5.01%; Cl: 11.02%; N: 13.06%; S: 9.96%.
Found: C: 40.67%; H: 4.97%; Cl: 11.21%; N: 12.72%; S: 9.45%.

5.

4-[N-(2-hydroxyethyl)]-ethylamino-2,6-dimethyl-3-nitropyridine hydrochloride 1.86 Grams (0.01 mol) of 4-chloro-2,6-dimethyl-3-nitropyridine, 1.78 g (0.02 mol) of 2-(ethylamino)-ethanol and 1 g (0.01 mol) of triethylamine are dissolved in 10 ml of isopropanol and heated at boiling point for 10 hours. Subsequently the mixture is concentrated, dissolved in water and shaken out twice with chloroform. The chloroform phase is dried and concentrated, the resulting base is dissolved in ethanol and converted into the hydrochloride with ethanolic hydrochloric acid.

Yield: 2.6 g (94.5% of the th.); melting point 116° to 118° C.

$C_{11}H_{18}Cl\ N_3O_3$ (MW=275.74)
Analysis:
Calculated: C: 47.92%; H: 6.58%; Cl: 12.86%; N: 15.24%;
Found: C: 47.89%; H: 6.68%; Cl: 13.01%; N: 15.03%;

6.

4-[N-(2-chloroethyl)]-ethylamino-2,6-dimethyl-3-nitropyridine hydrochloride

5 Milliliters of thionyl chloride are added dropwise to a solution of 2 g (0.0084 mol) of 4-[N-(2-hydroxyethyl)]-ethylamino-2,6-dimethyl-3-nitropyridine of Example 5 in 15 ml of chloroform, and the mixture is then heated for 1 hour at 70° C. After cooling, water is added, the mixture is neutralized with sodium bicarbonate and shaken out with chloroform. The chloroform phase is dried with sodium sulfate and concentrated. The oil obtained is converted with ethanolic hydrochloric acid into the hydrochloride.

Yield: 1.8 g (73.2% of the th.); melting point 175° to 179° C.

$C_{11}H_{17}Cl_2 N_3O_2$ (MW=294.18)

Analysis:

Calculated: C: 44.91%; H: 5.83%; Cl: 24.10%; N: 14.28%; Found: C: 45.03%; H: 5.94%; Cl: 24.28%; N: 14.37%;

7. 4-[N-(2-methylthioethyl)]-ethylamino-2,6-dimethyl-3-nitropyridine hydrochloride 0.48 Gram (0.012 mol) of sodium hydroxide is dissolved in 2 ml of water and diluted with 10 ml of ethanol; while cooling intensely with a freezing mixture, there is added first 0.58 g (0.012 mol) of methylmercaptan and subsequently there are added dropwise, within 10 minutes, 2.57 g (0.01 mol) of 4-[N-(2-chloroethyl)]-ethylamino-2,6-dimethyl-3-nitropyridine of Example 6 in 10 ml of ethanol. The mixture is then heated at 90° C. for another 2 hours. After cooling it is concentrated, dissolved in water and shaken out with chloroform. The chloroform phase is dried with sodium sulfate and concentrated. The residue is converted with ethanolic hydrochloric acid into the hydrochloride and recrystallized from isopropanol.

Yield: 1.6 g (52.5% of the th.); melting point 138° to 140° C.

$C_{12}H_{20}Cl N_3O_2S$ (MW=305.83)

Analysis:

Calculated: C: 47.13%; H: 6.59%; Cl: 11.59%; N: 13.74%; S: 10.48%;

Found: C 46.68%; H: 6.54%; Cl: 11.61%; N: 13.42%; S: 10.78%.

8. 4-Benzylamino-2,6-dimethyl-3-nitropyridine hydrochloride 9.3 Grams (0.05 mol) of 4-chloro-2,6-dimethyl-3-nitropyridine and 10.7 g (0.1 mol) of benzylamine are heated for 5 hours at boiling point in 20 ml of isopropanol. After cooling, the mixture is concentrated, dissolved in water and extracted with chloroform. The chloroform phase is dried with sodium sulfate and concentrated. The residue is converted with ethanolic hydrochloric acid into the hydrochloride and recrystallized from isopropanol.

Yield: 7.9 g (53.8% of the theory); melting point 192° to 193° C.

$C_{14}H_{16}Cl N_3O_2$ (MW=293.75)

Analysis:

Calculated: C: 57.24%; H: 5.49%; Cl: 12.07%; N: 14.31%. Found: C: 57.45%; H: 5.39%; Cl: 12.18%; N: 14.12%.

The above-mentioned compounds as well as those prepared in an analogous manner have been summarized in the following Table 1.

TABLE 1

| Example | R¹ | R² | R³ | R⁴ | Z | Y | isolated as | melting point °C. |
|---|---|---|---|---|---|---|---|---|
| 1 |  |  | —CH₃ | —CH₃ | H | NO₂ | HCl | 240 (Zers.) |
| 2 |  |  | —CH₃ | —CH₃ | Br | NO₂ | base | 138 |
| 3 |  |  | —CH₃ | —CH₃ | Br | NO₂ | HCl | 170 |
| 4 |  |  | —CH₃ | —CH₃ | H | NO₂ | HCl | 255 (decomp.) |
| 5 | —CH₂—CH₃ | —(CH₃)₂—OH | —CH₃ | —CH₃ | H | NO₂ | HCl | 116–118 |
| 6 | —CH₂—CH₃ | —(CH₂)₂—Cl | —CH₃ | —CH₃ | H | NO₂ | HCl | 175–179 |
| 7 | —CH₂—CH₃ | —(CH₂)₂—S—CH₃ | —CH₃ | —CH₃ | H | NO₂ | HCl | 138–140 |
| 8 | H | 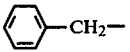 | —CH₃ | —CH₃ | H | NO₂ | HCl | 192–193 |
| 9 |  |  | —CH₃ | —CH₃ | H | NO₂ | HCl | 220–223 |
| 10 |  |  | —CH₃ | —CH₃ | H | NO₂ | 2 HCl | 260–265 (decomp.) |
| 11 |  |  | —CH₃ | —CH₃ | H | NO₂ | HCl | 240 |
| 12 |  |  | —CH₃ | —CH₃ | H | NO₂ | HCl | 240 |
| 13 |  |  | —CH₃ | —CH₃ | H | CN | HCl | 264–267 |

TABLE 1-continued

Compound according to formula I (cf. claim 1)

| Example | R¹ | R² | R³ | R⁴ | Z | Y | isolated as | melting point °C. |
|---|---|---|---|---|---|---|---|---|
| 14 | |  | —C₃H₇ | —C₃H₇ | H | NO₂ | HCl | 161–163 |
| 15 | | 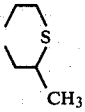 | —CH₃ | —CH₃ | H | —NO₂ | HCl | 215 (decomp.) |
| 16 | |  | —CH₃ | —CH₃ | H | NO₂ | base | 69 |
| 17 | H | 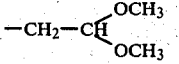 | —CH₃ | —CH₃ | H | NO₂ | base | 57 |
| 18 | H | —CH₂—CH₂—Cl | —CH₃ | —CH₃ | H | NO₂ | HCl | 177 |
| 19 | —CH₂—CH₃ | 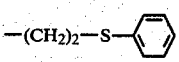 | —CH₃ | —CH₃ | H | NO₂ | HCl | 71–73 |
| 20 | H | 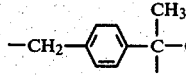 | —CH₃ | —CH₃ | H | NO₂ | HCl | 202–204 |
| 21 | H |  | —CH₃ | —CH₃ | H | NO₂ | HCl | 210–214 |
| 22 | H |  | —CH₃ | —CH₃ | H | NO₂ | | 188–190 |
| 23 | H |  | —CH₃ | —CH₃ | H | NO₂ | | 222–225 |
| 24 | H |  | —CH₃ | —CH₃ | H | NO₂ | HCl | 159–161 |
| 25 | H | 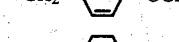 | —CH₃ | —CH₃ | H | NO₂ | HCl | 222–225 |
| 26 | H | 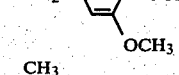 | —CH₃ | —CH₃ | H | NO₂ | HCl | 194–196 |
| 27 | H | 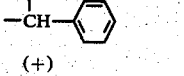 | —CH₃ | —CH₃ | H | NO₂ | HCl | 194–196 |
| 28 | H | 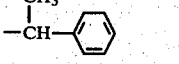 | —CH₃ | —CH₃ | H | NO₂ | base | 102–103 |
| 29 | H |  | —CH₃ | —CH₃ | H | NO₂ | base | 117–119 |
| 30 | |  | —C₆H₁₃ | —CH₃ | H | NO₂ | HCl | 202–204 (decomp.) |
| 31 | |  | H | —CH₃ | H | NO₂ | HCl | 213 (decomp.) |
| 32 | H | —CH₂—CH₂—F | —CH₃ | —CH₃ | H | NO₂ | HCl | 176 |
| 33 | H |  | —CH₃ | —CH₃ | H | NO₂ | base | 107–109 |

TABLE 1-continued

Compound according to formula I (cf. claim 1)

| Example | R¹ | R² | R³ | R⁴ | Z | Y | isolated as | melting point °C. |
|---|---|---|---|---|---|---|---|---|
| 34 | H | —CH₂—CH₂—Cl | —CH₃ | —CH₃ | H | CN | HCl | 200-202 |
| 35 | H | —CH₂—CH₂—CH₂—Cl | —CH₃ | —CH₃ | H | NO₂ | HCl | 150-152 |
| 36 | H | —CH₂—CH₂—S—⟨phenyl⟩ | —CH₃ | —CH₃ | H | NO₂ | HCl | 102-103 |
| 37 | H | —CH₂—CH₂—S—⟨phenyl⟩—F | —CH₃ | —CH₃ | H | NO₂ | HCl | 153-154 |
| 38 | H | —CH₂—CH₂—S—⟨phenyl⟩—Cl | —CH₃ | —CH₃ | H | NO₂ | HCl | 113-114 |
| 39 | H | —CH₂—⟨phenyl⟩—NH₂ | —CH₃ | —CH₃ | H | NO₂ | HCl | 142-144 |
| 40 | H | —CH₂—⟨phenyl⟩—OH | —CH₃ | —CH₃ | H | NO₂ | base | 170-172 |
| 41 | H | —CH₂—CH₂—S—⟨phenyl⟩ | —CH₃ | —CH₃ | H | CN | HCl | 161-162 |
| 42 | H | —CH₂—CH₂—S—⟨phenyl⟩—OCH₃ | —CH₃ | —CH₃ | H | NO₂ | HCl | 159-160 |
| 43 | H | —CH₂—CH₂—S—⟨phenyl⟩—CH₃ | —CH₃ | —CH₃ | H | NO₂ | HCl | 194-195 |
| 44 | H | —CH₂—CH₂—S—CH₃ | —CH₃ | —CH₃ | H | NO₂ | HCl | 103-104 |
| 45 | H | —CH₂—CH₂—S—⟨phenyl⟩—NH₂ | —CH₃ | —CH₃ | H | NO₂ | 2 HCl | 246-248 |

Pharmacological test and results

1. Bronchospasmolytic action

The testing of the compounds of the invention for their bronchospasmolytic action is essentially carried out by way of the test arrangement described by H. Konzett and R. Roessler (Arch.exp.Path. u. Pharmak. 195 (1940) 71), as compared with the known bronchospasmolytic agent theophylline-ethylene diamine, wherein the inhibition of experimental bronchial spasms—caused by the intravenous administration of spasmogenic amines, such as acetyl choline, histamine and serotonin—is examined in guinea pigs of either sex under urethane anaesthesia (1.25 g/kg i.p.).

The test substances were administered in an aqueous solution either by the intravenous (i.v.) or the intraduodenal (i.d.) route. Water-insoluble compounds were applied i.d. in carboxymethyl cellulose suspensions. The $ED_{50}$ values which designate the dose in mg/kg at which the spasm caused experimentally has been reduced to 50%, as compared with that of untreated animals, were determined graphically from the dose action curves.

2. Acute toxicity

The $LD_{50}$ values or the $LD_{50}$ ranges were determined according to common standards via the mortality occurring over 7 days with NMRI mice following a single intraperitoneal (i.p.) administration.

The results of these tests, which demonstrate the superiority of the compounds of formula I of the invention over the standard preparation theophylline-ethylene diamine (especially under consideration of the more favorable ratio of $LD_{50}$ to $ED_{50}$), have been summarized in the following Table 2.

TABLE 2

| Compound of Example | Way of application | Bronchospasmolytic action ($ED_{50}$ in mg/kg) as compared with | | | Toxicity $LD_{50}$ (mouse i.p.) mg/kg |
|---|---|---|---|---|---|
| | | acetyl choline | histamine | serotonin | |
| 1 | i.v. | 1.47 | 1.05 | 1.32 | 160* |
|   | i.d. | 4.13 | 2.6 | 2.52 | (145-177) |
| 9 | i.v. | 3-10 | 1-3 | | 300-1000 |
| 13 | i.v. | 3 | 1-3 | 3 | 150-300 |
|    | i.d. | 3-10 | 1-3 | | |
| 14 | i.v. | 1-3 | 3 | 3-10 | 300-600 |
| 15 | i.v. | 3-10 | 3-10 | | 150-300 |
| 17 | i.v. | 3-10 | >10 | | 400-800 |
| 18 | i.v. | 1-3 | 3 | 1-3 | 150-300 |
| 22 | i.v. | 3-10 | 3 | | |
| 23 | i.v. | 1-3 | 3-10 | | 600-1200 |
| 24 | i.v. | 1-3 | 0.3-1.0 | 1-3 | >600 |
| 32 | i.v. | 3-10 | 1 | 1-3 | 150-300 |
| theophylline-ethylene diamine | i.v. | 8.3 | 5.6 | 7.3 | 217* |
| | i.d. | 10-20 | | | (210-223) |

*determined acc. to Litchfield and Wilcoxon (J. Pharmacol. exp. Ther. 96 (1949) 99)

We claim:

1. 4-Aminopyridines of the formula

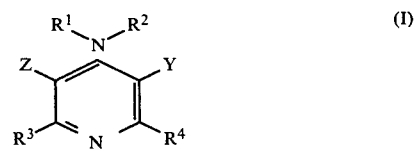

(I)

in which

R¹ is hydrogen or alkyl of up to 6 carbon atoms and
R² represents (a) alkyl of up to 6 carbon atoms substituted up to three times with at least one radical from the group of halogen and hydroxyl, with formyl acetalized with an alcohol of up to 3 carbon atoms, alkylthio of up to 3 carbon atoms, phenylthio or the corresponding alkyl- and phenylsulfoxy and sulfone groups, the phenyl ring optionally carrying in each case up to three substituents from the group of alkyl, alkyl halide, alkoxy, mono- or dialkylamino having each up to 4 carbon atoms in each alkyl radical, halogen, nitro, amino and hydroxy, or (b) phenylalkyl or diphenyl-alkyl of up to 6 carbon atoms in the linear or branched alkyl moiety, the phenyl rings optionally being substituted up to three times with at least one radical from the group of alkyl, alkoxy, alkyl halide with up to 4 carbon atoms each, halogen, amino, hydroxy, nitro, the sulfamoyl group and the methylene dioxy radical, or $R^1$ and $R^2$, together with the nitrogen atom present in the 4-position, form a five- to seven-membered heterocyclic ring optionally substituted with alkyl of up to 2 carbon atoms and including up to two hetero-atoms, the second hetero-atom being oxygen, sulfur optionally carrying up to two oxygen atoms, or nitrogen, and $R^3$ and $R^4$ which may be identical or different, each represent alkyl of up to 9 carbon atoms, one of the two radicals optionally also being hydrogen, Y is a nitro or a cyano group, and Z stands for hydrogen or halogen, and the physiologically acceptable salts of these compounds.

2. Compounds as claimed in claim 1 in which (a) in $R^2$ the alkyl moiety of the phenylalkyl or the diphenylalkyl radical includes up to 4 carbon atoms, (b) the alkyls of $R^3$ and $R^4$ each have up to 7, preferably up to 4 carbon atoms, or (c) a heterocyclic ring formed of $R^1$ and $R^2$ with the N-atom in the 4-position is saturated.

3. Compounds and the salts thereof as claimed in claim 1, wherein $R^1$ and $R^2$ together with the N-atom in the 4-position form a morpholine or thiomorpholine ring, and $R^3$ and $R^4$ each represent alkyl of up to 4 carbon atoms, and Z is hydrogen.

4. Compounds and the salts thereof as claimed in claim 1, wherein $R^1$ is hydrogen or alkyl of up to 4 carbon atoms, $R^2$ is alkyl of up to 4 carbon atoms substituted by halogen, alkylthio of up to 3 carbon atoms or by an optionally substituted phenylthio group, $R^3$ and $R^4$ each represent alkyl of up to 4 carbon atoms, and Z is hydrogen.

5. Compounds and the salts thereof as claimed in claim 1, wherein $R^1$ is hydrogen, $R^2$ is benzyl, the $CH_2$ group of which may be substituted by methyl and the phenyl ring of which may be substituted by alkoxy of up to 2 carbon atoms, halogen, the sulfamoyl group or the methylenedioxy radical, $R^3$ and $R^4$ each represent alkyl of up to 4 carbon atoms, and Z is hydrogen.

6. Bronchospasmolytic composition comprising a pharmaceutically effective amount of a compound as defined in claim 1 and a physiologically acceptable auxiliary agent or carrier therefor.

7. A method of treating a human patient having bronchospasms which comprises oral administration to said patient of an effective dosage of from about 30 to 150 mg/day of a compound as defined in claim 1.

8. A method of treating a human patient having bronchospasms which comprises intravenous administration to said patient of an effective dosage of from 10 to 50 mg/day of a compound as claimed in claim 1.

* * * * *